United States Patent [19]

Goetz et al.

[11] Patent Number: 4,933,477

[45] Date of Patent: Jun. 12, 1990

[54] PREPARATION OF PHENYL-SUBSTITUTED EPOXIDES

[75] Inventors: Norbert Goetz, Worms; Hans-Gert Recker, Ludwigshafen; Hubert Smuda, Heidelberg, all of Fed. Rep. of Germany

[73] Assignee: BASF Aktiengesellschaft, Ludwigshafen, Fed. Rep. of Germany

[21] Appl. No.: 236,216

[22] Filed: Aug. 25, 1988

[30] Foreign Application Priority Data

Sep. 2, 1987 [DE] Fed. Rep. of Germany ....... 3729226

[51] Int. Cl.$^5$ ............................................. C07D 301/02
[52] U.S. Cl. .................................... 549/519; 549/520; 549/522
[58] Field of Search ........................ 549/519, 520, 522

[56] References Cited

U.S. PATENT DOCUMENTS

| 2,237,284 | 4/1941 | Alquist et al. | 549/522 |
| 2,816,059 | 12/1957 | Mills | 549/519 |
| 2,887,509 | 5/1959 | Nash | 514/555 |

FOREIGN PATENT DOCUMENTS 252215 2/1967 Austria.

OTHER PUBLICATIONS

Wierenga et al, J. Org. Chem. 49 (1984), pp. 438–442.
Chapman et al, J. Chem. Soc. (C) 1967, pp. 293–296.

*Primary Examiner*—Glennon H. Hollrah
*Assistant Examiner*—Ba K. Trinh
*Attorney, Agent, or Firm*—Keil & Weinkauf

[57] ABSTRACT

Phenyl-substituted epoxides of the formula

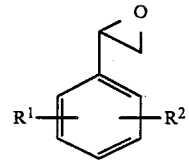

where $R^1$ and $R^2$ are each hydrogen, alkyl, alkenyl, phenyl, halogen, nitro, alkoxy, haloalkyl, phenoxy or phenylsulfonyl, are prepared by reducing a haloacetophenone to a halohydrin and reacting the halohydrin with an alkali metal hydroxide by a process in which the reduction with the alkali metal borohydride and the reaction are carried out in aqueous organic solution, or the cyclization of a halohydrin with an alkali metal hydroxide is carried out in an organic liquid.

5 Claims, No Drawings

PREPARATION OF PHENYL-SUBSTITUTED EPOXIDES

The present invention relates to a process for the preparation of phenyl-substituted epoxides.

Phenyl-substituted epoxides are useful intermediates for the preparation of antimycotic and fungicidal azolylmethyloxiranes. Such azolylmethyloxiranes and their preparation are described in European Patent Application 94,564.

The industrial production of phenyl-substituted epoxides, for example styrene oxide, is carried out, for example, by Friedel-Crafts alkylation of benzene with ethylene to give ethylbenzene, followed by dehydrogenation to styrene. The epoxidation can be effected by a subsequent gas-phase oxidation, by means of a peracid or by an addition reaction with hypochlorous acid with subsequent cyclization (cf. for example K. Weissermel, H. J. Arpe: Industrielle organische Chemie, 2nd Edition, pages 256 and 318–321, Verlag Chemie, Weinheim, and Org. Synth. Coll. Vol. I, 494 (1948)).

If selectively substituted phenyl epoxides are desired, the route via Friedel-Crafts alkylation will be avoided since this reaction normally leads to product mixtures. These mixtures are generally difficult to separate and therefore cannot be used for the industrial production of these compounds.

Better starting materials are therefore the substituted benzaldehydes and substituted omega-haloacetophenones, which can be synthesized with good selectivity.

Starting from benzaldehyde, the associated epoxide can be produced, for example, by reaction with the anion of a trimethylsulfonium halide (cf. for example V. Franzen and H.E. Driesen, Chem. Ber. 96 (1963), 1881). However, the benzaldehydes are frequently obtainable only in moderate yield (cf. for example Olaah et al., Acta Chim. Hung. 7 (1955), 89; Lock et al., Chem. Ber. 72 (1939), 1064; Brown et al., J. Chem. Soc. 1949, Suppl. 95, 99; and Hass et al., J. Amer. Chem. Soc. 71 (1949), 1767).

Starting from substituted omega-haloacetophenones, which can be obtained in good to very good yield, the associated epoxides are obtainable by reduction of the carbonyl group to the halohydrin by means of suitable reagents, such as aluminum triisopropylate according to Meerwein, Ponndorf and Verley (cf. Organikum, 11th Edition, 1972, page 539 and C.O. Guss, J. Org. Chem. 17 (1952), 678), or an alkali metal borohydride or alkaline earth metal borohydride. (cf.
Knipe, J. Chem. Soc. Perkin Trans. II, (1973), 589
A.P. Bossetti and D.R. Crist, J. Heterocycl. Chem. 12 (1975), 1287
H. Jopff and R. Wandeler, He(v. Chim. Acta XLV (1962) 982
M. Sato, A Kosasayama and Uchimaru, Chem. Pharm. Bull. 29 (1981), 2885
C. Guss, J. Org. Chem. 17 (1952), 678
J. F. Nash, U.S. Pat. No. 2,887,509
W. Wierenga, A. W. Harrison, B. R. Evans and C. G. Chidester, J. Org. Chem. 49 (1984), 438
L. Almiranze and W. Murmann, Austrian Pat. No. 252,215
Continental Pharma, Belgian Pat. No. 877,694
Hoffmann-La Roche, French Pat. No. 1,381,639
N. B. Chapman, K. Clarke, R. M. Pinder and S. N. Shawney, J. Chem. Soc. (C) (1967), 293
S. Sorriso. Z. Naturforsch. B 32 (1977), 1467 A. Huth and
F. Neubauer, Liebigs Ann. Chem. 56 (1979) Ciba-Geigy, European Pat. No. 69,838
Kiernan, J. A. and Baker, P. K., European Pat. No. 0,026,298 Abenheim, Henry-Basch, Freon, Bull. Soc. Chim. Fr. (1970) 179).

Subsequent cyclization by means of alkali metal hydroxides or alkaline earth metal hydroxides leads to the desired epoxide (see equation)

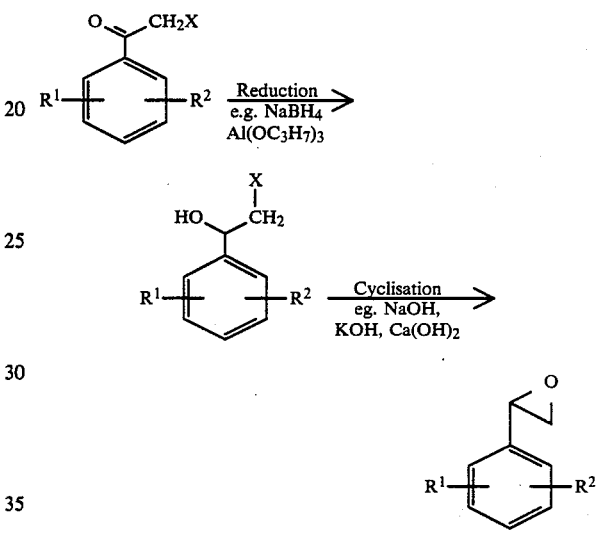

Since it is known that omega-haloketones undergo many side reactions under the action of hydroxyl ions in protic solvents, for example hydrolysis of the omega-halogen atom (cf. R. Verhe and N. DeKimpe in S. Patai (ed.): The Chemistry of Functional Groups, Suppl. D, Part 1: Halides, Pseudo-Halides and Azides, J. Wiley & Sons, 1983, page 850 et seq. and the literature cited therein), the technical literature describes the two reaction steps, reduction and cyclization, in the procedure in protic solvents as being carried out in succession in this order and separately from one another (cf. A. C. Knipe, J. Chem. Soc. Perkin Trans. II, (1973), 589 A.P. Bossetti and D. R. Crist, J. Heterocycl. Chem. 12 (1975), 1287
H. Hopff and R. Wandeler, Helv. Chim. Acta XLV (1962) 982
M. Sato, A. Kosaayama and F. Uchimaru, Chem. Pharm. Bull 29 (1981), 2885
C. Guss, J. Org. Chem. 17 (1970), 678
J. S. Nash, U.S. Pat. No. 2,887,509
W. Wierenga, A. W. Harrison, B. R. Evans and C. G. Chidester, J. Org. Chem. 49 (1984), 438
L. Almiranze and W. Murmann, Austrian Pat. No. 252,215 Continental Pharma, Belgian Pat. No. 877,694
Hoffmann-La Roche, French Pat. No. 1,381,639 N. B. Chapman, K. Clarke, R. M. Pinder and S. N. Shawney, J. Chem. Soc. (C) (1967), 293.
S. Sorriso, Z. Naturforsch. B 32 (1977), 1467
A. Huth and F. Neubauer, Liebigs Ann. Chem. 56 (1979) Ciba-Geigy, European Pat. No. 69,838

Kiernan, J. A. and Baker, P. K., European Pat. No. 0,026,298 Abenheim, Henry-Basch, Freon, Bull. Soc. Chim. Fr. (1970), 179).

This applies both to the reduction according to Meerwein, Ponndorf and Verley and to the reduction with sodium borohydride. Dilute reagent solutions, for example 2N NaBH₄ solution and 2N KOH solution (cf. for example N. B. Chapman, K. Clarke, R. M. Pinder and S. M. Sawhney, J. Chem. Soc. C, 1967, 293) are used. For the procedure with sodium borohydride in protic solvents, the following stoichiometric ratios are recommended in the technical literature (based on reduction equivalents of borohydride):

| Molar ratio of omega-haloacetophenone to sodium borohydride | Excess of reduction equivalents | Literature |
| --- | --- | --- |
| 1.72:2.43 | 5,6-fold | U.S. Pat. No. 2,887,509 |
| 1.63:0.78 | 2-fold | AU-25 22 15 |
| 0.1:0.11 | 4-fold | BE-877 694 |
| 0.04:0.05 | 4-fold | N. B. Chapman et al J. Chem. Soc. (C) (1967) 293 |
| 0.096:0.063 | 2,6-fold | S. Sorriso, Z. Naturforsch. B 32, (1977) 1467 |
| 0.11:0.21 | 7,6-fold | E.P. 26 298 |

Accordingly, the skilled worker must assume that the reducing agent will undergo decomposition reactions under the reaction conditions used.

The known processes are disadvantageous in that a large excess of reducing agent is used there, an additional step of extractive separation (isolation of the halohydrin from the reduction mixture) is required, the solvent has to be changed or mixtures of epoxides and halohydrin, which have not been described in detail, are obtained (cf. J. F. Nash, U.S. Pat. No. 2,887,509 and C. O. Guss, J. Org. Chem. 17 (1952), 678).

It is an object of the present invention to provide a simple and economical process for the preparation of phenyl-substituted epoxides in high yields.

We have found that this object is achieved by a process for the preparation of phenyl-substituted epoxides of the formula I

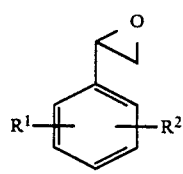

where $R^1$ and $R^2$ are identical or different and are each hydrogen, $C_1$-$C_4$-alkyl, $C_1$-$C_4$-alkenyl, phenyl, halogen, nitro, $C_1$-$C_4$-alkoxy, $C_1$-$C_4$-haloalkyl, phenoxy or phenylsulfonyl, by reducing a haloacetophenone of the formula II

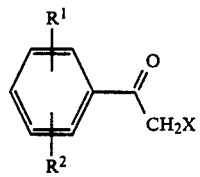

where $R^1$ and $R^2$ have the abovementioned meanings and X is a halogen atom, with an alkali metal borohydride, alkaline earth metal borohydride or quaternary ammonium borohydride to give a halohydrin of the formula III

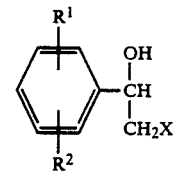

where $R^1$, $R^2$ and X have the abovementioned meanings, and reacting the halohydrin with an alkali metal hydroxide or alkaline earth metal hydroxide, wherein the reduction of the haloacetophenone and the reaction of the halohydrin are carried out in a mixture of water, a water-miscible organic liquid and, if required, a water-immiscible organic liquid.

The haloacetophenone is used, for example, in the form of the solid substance or in the form of its solution in a water-miscible or water-immiscible organic liquid, and is reacted with a concentrated solution or suspension of an alkali metal hydroxide or alkaline earth metal hydroxide in a mixture of water and a water-miscible organic liquid. Suitable organic liquids for this purpose are water-miscible alcohols, amides, nitriles, sulfoxides, sulfones, ureas and ethers.

A solution of a mixture of an alkali metal borohydride and an alkali metal hydroxide in a mixture of water and a water-miscible organic liquid is preferably reacted with a solution of the haloacetophenone in an organic liquid.

We have found, surprisingly, that the known side reactions of the omega-haloacetophenones are not observed in this procedure, and the phenyl-substituted epoxides are obtained in good to very good yield. The novel process can be used in particular to prepare compounds of the formula I in which $R^1$ and $R^2$ are not simultaneously hydrogen.

The novel process as claimed in claim 1 can be carried out continuously or batchwise, for example in a stirred kettle. The reaction is advantageously effected at, for example from +10° to +60° C., preferably from +10° to +40° C., particularly preferably from +20° to +40° C.

The end product can be isolated from the reaction mixture by a conventional method of preparative organic chemistry, for example by extraction followed by distillation or recrystallization using an organic solvent. For the extraction, the pH of the aqueous phase can be brought to 2-14 by adding an acid, for example a 10-100, preferably 20-50, % strength acid. We have found, surprisingly, that the yield in the extraction is dependent on the pH of the aqueous phase, so that the pH is particularly preferably brought to 4-9 or 12-14.

The omega-haloacetophenone of the formula II can be used in the form of a solid substance or in the form of a solution in a water-miscible or water-immiscible organic solvent. Since, in carrying out industrial processes, liquids are easier to handle than solid substances, solutions are generally preferred. The concentrations of the solutions can be, for example, from 5% by weight to the saturation concentration of haloacetophenone, the saturated solutions being preferably used. The preferred water-miscible organic solvents include alcohols, such as methanol, ethanol, isopropanol, n-propanol, n-butanol, sec-butanol, tert-butanol, ethylene glycol, propylene glycol and glycerol, as well as cyclic amides, such as N-methylpyrrolidone, nitriles, such as acetonitrile, sulfoxides and sulfones, such as dimethyl sulfoxide or sulfolane, urea derivatives, such as 1,3-dimethyl-3,4,5-tetrahydro-2(1H)-pyrimidone (DMPU), and ethers, such as tetrahydrofuran or glycol ether, and mixtures of these liquids.

The preferred water-immiscible organic solvents include alcohols, eg. benzyl alcohol, pentanol, cyclohexanol and cyclopentanol, halohydrocarbons, eg. methylene chloride, chloroform, carbon tetrachloride, dichloroethane, chlorobenzene and fluorobenzene, hydrocarbons, such as naphtha, toluene, benzene, xylene, cyclohexane, pentane, hexane, heptane and octane, and ethers, eg. methyl tert-butyl ether.

Examples of suitable bases are alkali metal hydroxides, such as lithium hydroxide, sodium hydroxide or potassium hydroxide, with or without the addition of a phase transfer catalyst (cf. E. V. Dehmlow and S. S. Dehmlow, Phase Transfer Catalysis, Verlag Chemie 1980). Other suitable compounds are, for example, alkaline earth metal hydroxides, such as magnesium hydroxide, calcium hydroxide, strontium hydroxide or barium hydroxide. Sodium hydroxide and potassium hydroxide and calcium hydroxide in the form of their aqueous solutions or suspensions in a concentration of, for example, from 20 to 60, preferably from 28 to 50, % by weight are particularly preferably used.

Examples of suitable reducing agents are the alkali metal and alkaline earth metal tetrahydridoborates, but alkoxy-substituted or cyano-substituted tetrahydridoborates can also be used. Sodium tetrahydridoborate (sodium boranate, NaBH4) is preferably used, particularly preferably in the form of a 6.6-22.5% strength by weight NaBH4 solution in 28-50% strength by weight aqueous NaOH solution.

The reducing agents are preferably used in stoichiometric amounts, based on the omega-haloacetophenone of the formula II, but up to twice the stoichiometric amount may also be used.

The bases are preferably employed in stoichiometric amounts, based on the omega-haloacetophenone of the formula II, but up to twice the stoichiometric amount may also be used.

The single-stage process permits phenyl-substituted epoxides of the formula I to be synthesized in an industrially advantageous manner since an extractive working-up step for the halohydrin is dispensed with.

In the process for the preparation of phenyl-substituted epoxides of the formula I as claimed in claim 2, a halohydrin of the formula III is treated with a suspension of an alkali metal hydroxide or alkaline earth metal hydroxide in a dipolar, aprotic organic liquid.

The process as claimed in claim 2 can be carried out continuously or batchwise, for example in a stirred kettle. The reaction is advantageously carried out at from +10° to +60° C., preferably from +10° to +40° C., particularly preferably from +20° to +40° C.

The end product can be isolated from the reaction mixture by a conventional method of preparative organic chemistry, for example by pouring into water and extraction followed by distillation or recrystallization using a solvent.

The required halohydrin of the formula III can be used in the form of the solid substance or in the form of a solution in a dipolar, aprotic organic solvent. Since, in carrying out industrial processes, liquids are easier to handle than solid substances, solutions are preferred. The concentration of the solutions can be from 5% by weight to the saturation concentration of halohydrin, the saturated solutions being preferably used.

The preferred dipolar, aprotic solvents include ethers, such as tetrahydrofuran, methyl tert-butyl ether, dimethyl glycol ether or polyglycol methyl ether, as well as amides, such as dimethylformamide or dimethylacetamide, nitriles, such as acetonitrile, sulfoxides, such as dimethyl sulfoxide, sulfones, such as sulfolane, and urea derivatives, such as 1,3-dimethyl-3,4,5-tetrahydro2(1H)-pyrimidone (DMPU) and mixtures of these liquids.

Examples of suitable bases are alkali metal hydroxides, such as lithium hydroxide, sodium hydroxide or potassium hydroxide, with or without the addition of a phase transfer catalyst. Alkaline earth metal hydroxides, such as magnesium hydroxide, calcium hydroxide, strontium hydroxide and barium hydroxide, are also suitable. Sodium hydroxide, potassium hydroxide and calcium hydroxide are particularly preferred. The hydroxides are insoluble in the dipolar, aprotic liquids and are therefore used in the form of their suspensions.

The liquids are used in dry form, so that the presence of water is substantially excluded. The water contents of the solvents must not be more than 1% by weight, based on the total organic liquid.

The bases are preferably used in stoichiometric amounts, based on the halohydrin of the general formula III, but up to 10 times the stoichiometric amount may also be used.

In the compounds of the formula I, $R^1$ and $R^2$ may be identical or different and are each preferably hydrogen, methyl, ethyl, propyl, isopropyl, butyl, sec-butyl, isobutyl, tert-Ltyl, phenyl, 2-chloro, 3-chloro, 4-chloro, 2-fluoro, 3-fluoro, 4-fluoro, 4-bromo, 2-fluoro-6-chloro, 2,4-dichloro, 3,4-dichloro, 3,5-dichloro, 2,6-dichloro, 3-chloro-4-methyl, 2-methoxy, 3-methoxy, 2,4-dimethoxy, 3,4-dimethoxy, 4-methoxy, 4-ethoxy, 4-tertbutoxy, 4-phenoxy, 3-phenoxy, 3-nitro, 4-nitro, 3-trifluoromethyl, 4-trifluoromethyl or 4phenylsulfonyl.

$R^1$ and $R^2$ are particularly preferably each hydrogen, 2-chloro, 4-chloro, 2-fluoro, 3-fluoro, 4-fluoro, 2-fluoro-6-chloro, 4-bromo, 2,4-dichloro or halomethyl, with the proviso that $R^1$ and $R^2$ are not simultaneously hydrogen.

The phenyl-substituted epoxides can be subjected to a rearrangement reaction over a silica catalyst to give the corresponding phenylacetaldehydes

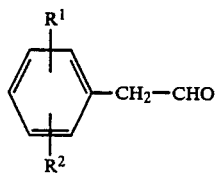

which can be condensed with an aldehyde to give an acrolein

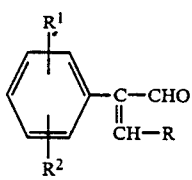

These can be oxidized, for example with $H_2O_2$, to give a formyloxirane

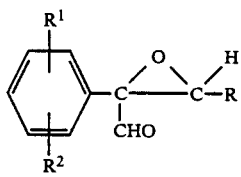

which can be converted by reduction, for example with $NaBH_4$, into a hydroxymethyloxirane

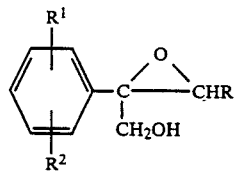

which is suitable for the conversion into azolylmethyloxiranes which is described in European Pat. No. 94,564.

Preparation methods

EXAMPLE 1

4-fluorophenyloxirane (p-fluorostyrene oxide)

0.52 mole of sodium boronate is dissolved at room temperature in a solution of 2.1 moles of alkali metal hydroxide or a suspension of 1.1 moles of alkaline earth metal hydroxide in 200 ml of water under an $N_2$ atmosphere. This solution is cooled in a water bath. Thereafter, 10–800 ml of an alcohol (see Table 1) are added sufficiently slowly to prevent the temperature from exceeding 35° C. After the components have been completely mixed, the mixture is cooled to 20° C. and 345 g (2 moles) of omega-chloro-p-fluorophenylacetophenone in the form of a 20–70% strength by weight solution, preferably a saturated solution, in a water-immiscible or water-miscible organic solvent (see Table 1) are then added sufficiently slowly to prevent the internal temperature of the reaction mixture from exceeding 55° C. When the addition is complete, stirring is continued for from 2 minutes to 6 days.

Working up

A. If water-miscible, organic solvents are used:

200–400 ml of a water-immiscible organic solvent (eg. toluene) are added. The pH of the aqueous phase is brought to 4–14, preferably 7, with 10–100% strength acid, preferably 50% strength sulfuric acid. After phase separation from the aqueous solution, the organic phase is distilled. The organic solvents which pass over initially can be reused. The end product can be distilled under different pressures in the same apparatus or by means of a thin film evaporator. Yields are shown in Table 1.

B. If water-immiscible, organic solvents are used:

100–400 ml of water are added to the mixture. The pH of the aqueous phase is brought to 4–14, preferably 7, with an acid as under A. The aqueous phase is separated off and the organic phase is distilled. The organic solvents which initially pass over can be reused. The end product can be distilled under different pressures in the same apparatus or by means of a thin film evaporator.

TABLE 1 of 4-fluorophenyloxirane (bp. = 91–93° C./24) corresponding to Example 1

| Batch | Amount and type of base | Amount of NaBH₄ | Alcohol component (water-miscible) | Solvent for acetophenone (water-immiscible except for 13) | Temp. | Reaction time | Yield (% by wt.) after distillation based on haloacetophenone |
|---|---|---|---|---|---|---|---|
| 1 | 84 g NaOH | 19 g | 286 ml Isopropanol | 300 ml CH₂Cl₂ | RT (20° C.) | 4 h | 96 |
| 2 | 81 g Ca(OH)₂ | 19 g | 400 ml Methanol | 700 ml CH₂Cl₂ | RT | 14 h | 90 |
| 3 | 81 g Ca(OH)₂ | 19 g | 400 ml Methanol | 350 ml CH₂Cl₂ | RT | 14 h | 89 |
| 4 | 81 g Ca(OH)₂ | 19 g | 400 ml · Methanol | 350 ml CH₂Cl₂ | RT | 12 h | 96 |
| 5 | 91 g Ca(OH)₂ | 19 g | 400 ml | 690 ml toluene | RT | 14 h | 93 |

TABLE 1-continued of 4-fluorophenyloxirane (bp. = 91–93° C./24) corresponding to Example 1

| Batch | Amount and type of base | Amount of NaBH₄ | Alcohol component (water-miscible) | Solvent for acetophenone (water-immiscible except for 13) | Temp. | Reaction time | Yield (% by wt.) after distillation based on halo-acetophenone |
|---|---|---|---|---|---|---|---|
| 6 | 81 g Ca(OH)₂ | 19 g | Methanol 400 ml | 690 ml toluene | RT | 14 h | 96 |
| 7 | 81 g Ca(OH)₂ | 19 g | Methanol 400 ml | 690 ml toluene | Reflux (80° C.) | 1 h | 84 |
| 8 | 84 g NaOH | 19 g | Methanol 300 ml | 172 ml CH₂Cl₂ | RT | 1 h | 96 |
| 9 | 84 g NaOH | 19 g | Methanol 40 ml | 172 ml CH₂Cl₂ | RT | 15 min | 86 |
| 10 | 118 g KOH | 19 g | Methanol 150 ml | 300 ml toluene | RT | 30 min | 94 |
| 11 | 160 g NaOH | 37.5 g | Methanol 400 ml | 600 ml toluene | RT | 1 h | 88 |
| 12 | 84 g NaOH | 19 g | Methanol 400 ml | 400 ml fluoro-benzene | RT | 1 h | 92 |
| 13 | 84 g NaOH | 19 g | — | 400 ml methanol; toluene for working up | RT | 4 h | 82 |

TABLE 2

The compounds listed in Table 2 below were prepared according to Example 1, batch 8.

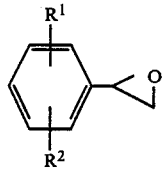

| Example No. | R¹ | R² | Physical data | Yield (% by weight) (based on haloaceto-phenone) |
|---|---|---|---|---|
| 2 | p-OCH₃ | H | mp. 23° C. | 86 |
| 3 | p-Cl | H | bp. 74–76° C./0.8 | 88 |
| 4 | p-CH₃ | H | bp. 51–53° C./1.0 | 89 |
| 5 | m-OCH₃ | H | bp. 76–79° C./0.8 | 85 |
| 6 | m-NO₂ | H | bp. 110–112° C./0.7 | 92 |
| 7 | p-NO₂ | H | mp. 83° C. (petroleum ether) | 88 |
| 8 | p-Br | H | 72–74° C./0.7 | 94 |
| 9 | m-NO₂ | H | bp. 94–97° C./1.0 | 92 |
| 10 | 3-F | 4-F | bp. 55–57° C./0.3 | 86 |
| 11 | o-NO₂ | H | mp. 60–62° C. (ether/petroleum ether) | 88 |
| 12 | 2-F | 4-F | bp. | 79 |

TABLE 2-continued

The compounds listed in Table 2 below were prepared according to Example 1, batch 8.

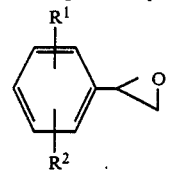

| Example No. | R¹ | R² | Physical data | Yield (% by weight) (based on haloaceto-phenone) |
|---|---|---|---|---|
| | | | 44–45° C./0.2 | |

EXAMPLE 13

Preparation of 4-fluorophenyloxirane (p-fluorostyrene oxide)

611 g of 1-(p-fluorophenyl)-2-chloroethanol are (Table 3, Example No. 15) added dropwise, in the course of 1 hour at 20° C. with thorough stirring and slight cooling, to 266 g (6.65 moles) of sodium hydroxide which are suspended in 1,700 ml of a dipolar aprotic organic solvent (cf. Table 3). The reaction mixture is then poured into ice water, the organic components are extracted with methylene chloride and the methylene chloride extract is dried over solid sodium sulfate. The crude product is purified by distillation.

TABLE 3

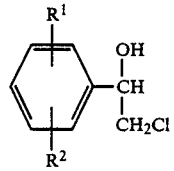

| Example No. | R¹ | R² | Dipolar aprotic solvent | Physical data | Yield (% by weight) (based on halohydrin) |
|---|---|---|---|---|---|
| 14 | p-Cl | H | Methyl-tert-butyl ether | bp. 70–72° C./0.2 | 87 |
| 15 | p-F | H | Tetrahydrofuran | bp. 62–63° C./0.3 | 83 |
| 16 | 4-F | 3-F | Tetrahydrofuran | bp. 55–57° C./0.3 | 85 |

TABLE 3-continued

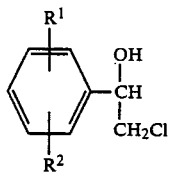

| Example No. | R[1] | R[2] | Dipolar aprotic solvent | Physical data | Yield (% by weight) (based on halohydrin) |
|---|---|---|---|---|---|
| 17 | 4-F | 2-F | Tetrahydrofuran | bp. 44–45° C./0.2 | 78 |

We claim:

1. A process for the preparation of a phenyl-substituted epoxide of the formula I

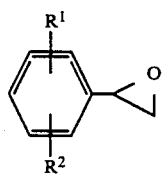

where $R^1$ and $R^2$ are identical or different and are each hydrogen, $C_1$-$C_4$-alkyl, $C_1$-$C_4$-alkenyl, phenyl, halogen, nitro, $C_1$-$C_4$-alkoxy, $C_1$-$C_4$-haloalkyl, phenoxy or phenylsulfonyl, which comprises: reducing a haloacetophenone of the formula II

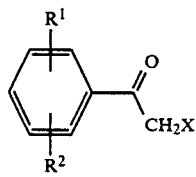

where $R^1$ and $R^2$ have the abovementioned meanings and X is a halogen atom, with from 1 to 2 equivalents based on the haloacetophenone of an alkali metal borohydride, alkaline earth et al borohydride or quaternary ammonium borohydride to give a halohydrin of the formula III

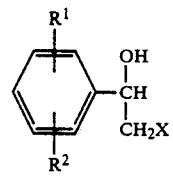

where $R^1$, $R^2$ and X have the abovementioned meanings, and reacting the halohydrin with an alkali metal hydroxide or alkaline earth metal hydroxide, wherein the reduction of the haloacetophenone and the reaction of the halohydrin are carried out simultaneously in a mixture of water, a water-miscible organic liquid and a water-immiscible organic liquid.

2. The process of claim 1, wherein an epoxide of the formula I is prepared, in which $R^1$ is hydrogen, halogen or $C_1$-$C_4$-haloalkyl and $R^2$ is halogen or $C_1$-$C_4$-haloalkyl.

3. The process of claim 1, wherein the reaction is carried out at from 10° to 60° C.

4. The process as claimed in claim 1, wherein the reaction mixture is worked up by extraction at a pH of 12–14 or 4–9.

5. The process of claim 1, wherein a compound of the formula I is prepared in which $R^1$ is 4-fluoro and $R^2$ is hydrogen.

* * * * *

UNITED STATES PATENT AND TRADEMARK OFFICE
CERTIFICATE OF CORRECTION

PATENT NO. : 4,933,477

DATED : June 12, 1990

INVENTOR(S) : Norbert GOETZ et al.

It is certified that error appears in the above-identified patent and that said Letters Patent is hereby corrected as shown below:

Claim 1, Col. 11, Line 47

"alkaline earth et al" should read
--alkaline earth metal--

Signed and Sealed this

Thirteenth Day of August, 1991

Attest:

HARRY F. MANBECK, JR.

Attesting Officer

Commissioner of Patents and Trademarks